United States Patent
Takagi et al.

(10) Patent No.: US 9,352,085 B2
(45) Date of Patent: May 31, 2016

(54) MEDICAL DEVICE

(71) Applicant: TERUMO KABUSHIKI KAISHA, Shibuya-ku (JP)

(72) Inventors: Toshiaki Takagi, Ashigarakami-gun (JP); Yousuke Ootani, Ashigarakami-gun (JP); Yusuke Sekine, Ashigarakami-gun (JP); Ryuusuke Takashige, Ashigarakami-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 668 days.

(21) Appl. No.: 13/724,814

(22) Filed: Dec. 21, 2012

(65) Prior Publication Data

US 2013/0116622 A1 May 9, 2013

Related U.S. Application Data

(63) Continuation of application No. PCT/JP2011/063130, filed on Jun. 8, 2011.

(30) Foreign Application Priority Data

Jun. 23, 2010 (JP) .................................. 2010-142338

(51) Int. Cl.
*A61M 37/00* (2006.01)
*A61M 5/32* (2006.01)
(Continued)

(52) U.S. Cl.
CPC ............ *A61M 5/158* (2013.01); *A61M 25/0043* (2013.01); *A61M 25/0084* (2013.01); *A61M 2025/0079* (2013.01); *A61M 2025/0092* (2013.01)

(58) Field of Classification Search
CPC ................. A61M 25/0084; A61M 2025/0079; A61M 2025/0092; A61M 25/0043; A61M 25/00; A61M 25/0067; A61M 25/0082; A61M 2025/0096; A61M 2025/0087; A61M 2025/0089; A61M 25/0074; A61M 25/0075; A61M 5/00; A61M 5/14; A61M 5/158
USPC ........................................................ 604/131
See application file for complete search history.

(56) References Cited

U.S. PATENT DOCUMENTS

| 5,693,029 | A | 12/1997 | Leonhardt |
| 6,547,767 | B1 * | 4/2003 | Moein ............................ 604/264 |
| 2006/0025720 | A1 | 2/2006 | Sawa et al. |

FOREIGN PATENT DOCUMENTS

| EP | 2 065 069 A1 | 6/2009 |
| EP | 2065069 A1 * | 6/2009 |

(Continued)

OTHER PUBLICATIONS

Notification of Transmittal of Translation of the International Preliminary Report on Patentability (Forms PCT/IB/338 and PCT/IB/373) and the Written Opinion of the International Searching Authority (Form PCT/ISA/237) issued on Jan. 24, 2013, by the International Bureau of WIPO in corresponding International Application No. PCT/JP2011/063130. (6 pages).

(Continued)

*Primary Examiner* — Jason Flick
(74) *Attorney, Agent, or Firm* — Buchanan Ingersoll & Rooney PC (57) ABSTRACT

A medical device includes a catheter having an opening formed in a side portion of the catheter, an infusion tubing extending within the catheter along an axial direction of the catheter; an infusion needle disposed at a distal portion of the infusion tubing, a connecting part which bendably connects the infusion needle to the distal portion of the infusion tubing, and a bending unit by which the infusion needle located inside the catheter so as to face the opening is bent at the connecting part at essentially a right angle with respect to the distal portion of the infusion tubing.

24 Claims, 6 Drawing Sheets

(51) Int. Cl.
*A61M 5/158* (2006.01)
*A61M 25/00* (2006.01)

(56) References Cited

FOREIGN PATENT DOCUMENTS

| | | | |
|---|---|---|---|
| JP | 5-261062 | A | 10/1993 |
| JP | 2003-339874 | A | 12/2003 |
| JP | 2004-329485 | A | 11/2004 |

OTHER PUBLICATIONS

International Search Report (PCT/ISA/210) issued on Jul. 12, 2011, by the Japanese Patent Office as the International Searching Authority for International Application No. PCT/JP2011/063130.
Office Action (Notification of Reasons for Refusal) issued on Dec. 22, 2015, by the Japanese Patent Office in corresponding Japanese Patent Application No. 2012-521399. (5 pages).

* cited by examiner

MEDICAL DEVICE

CROSS REFERENCES TO RELATED APPLICATIONS

This application is a continuation of International Application No. PCT/JP2011/063130 filed on Jun. 8, 2011 and claims priority to Japanese Application No. 2010-142338 filed on Jun. 23, 2012, the entire content of both of which is incorporated herein by reference.

TECHNICAL FIELD

The present invention generally relates to a medical device, particularly to a medical device which has an infusion needle in a catheter and by which a drug solution or a therapeutic substance is infused at a site of medical treatment in human tissue.

BACKGROUND DISCUSSION

As a medical device for applying a medical treatment to a local part in a living body, conventionally, there has been known a medical treatment device wherein an infusion needle is disposed in a lumen of a catheter so as to be able to move forward and backward, the catheter is inserted into the local part or the vicinity thereof, and a drug solution is infused from a distal portion of the infusion needle into the local part.

For instance, Patent Document 1 discloses a drug solution infusing medical treatment device wherein a drug solution is infused by projecting an infusion needle to a lateral side of a catheter inserted in a blood vessel. In this medical treatment device, the catheter is inserted in the blood vessel, and a pair of balloons disposed at a predetermined interval along a forward-backward direction is both inflated, whereby a sealed region closed at both ends thereof is formed in the blood vessel. After forcibly draining blood from the sealed region, the infusion needle is projected out via an opening formed in a catheter side wall between the pair of balloons to puncture a blood vessel wall, and, in this state, the drug solution is infused via a distal portion of the infusion needle.

An inside portion of a lumen of the catheter on the forward side of the opening through which to project the infusion needle is closed with a core member formed at a rear end thereof with a curved-surface guide part inclined with respect to an axial direction of the catheter, and the curved-surface guide part is disposed adjacent to the opening in the catheter side wall. Therefore, when a drug solution infusion tubing formed at a distal end thereof with the infusion needle is moved forward along the lumen of the catheter, the distal portion of the infusion needle makes contact with the curved-surface guide part and, further, is guided by the curved-surface guide part, to be projected via the opening in the catheter side wall to the outside of the catheter.

PRIOR ART DOCUMENT

Patent Document

Patent Document 1: Japanese Patent Laid-open No. 2003-339874

SUMMARY

However, since the projection of the infusion needle is guided by the curved-surface guide part in the inclined state relative to the axial direction of the catheter, the distal portion of the infusion needle projected to a lateral side of the catheter would be inclined, instead of being set at a right angle, with respect to the axial direction of the catheter. Furthermore, this results in that the position of the distal portion of the infusion needle thus projected would be varied in both the axial direction and a radial direction of the catheter according to the amount of movement of the drug solution infusion tubing relative to the catheter. Accordingly, it is difficult to position the distal portion of the infusion needle to a desired part, and it may not be possible to accurately infuse the drug solution to the local part needing administration of the drug. Especially, in medical treatment of a brain region, also for minimizing damage to a brain tissue arising from the puncture with the infusion needle, it has been desired to project the distal portion of the infusion needle at right angle with respect to the axial direction of the catheter.

The disclosure here describes a medical device by which a drug solution or a medical treatment substance such as neurotrophic factors, signal transduction substances, genes and cells can be infused to a site of medical treatment in a human tissue, by projecting a distal portion of an infusion needle at essentially a right angle with respect to an axial direction of a catheter.

The disclosed medical device is useful, for example, in blood vessel treatment, organ treatment, otorhinolaryngological treatment, and surgery, and is particularly useful for medical treatment applied to a brain region. Here, the medical treatment applied to the brain region includes a method in which a catheter is inserted via an opening formed in a part of the cranial bones to approach the brain tissue, and a method in which a catheter is inserted through a nostril to approach the brain tissue.

The medical device includes: a catheter having an opening formed in a side portion of the catheter; an infusion tubing extending within the catheter in an axial direction of the catheter, the infusion tubing possessing a distal portion; an infusion needle disposed at the distal portion of the infusion tubing; a bendable connecting part connecting the infusion needle to the distal portion of the infusion tubing; and bending means for bending the infusion needle, located inside the catheter in facing relation to the opening, at the connecting part at substantially a right angle with respect to the distal portion of the infusion tubing.

The bending means can be in the form of a first inflatable-and-contractible member which in a contracted state is disposed inside the catheter so as to face the opening with the infusion needle between the opening and the inflatable-and-contractible member. When the inflatable-and-contractible member is inflated, the inflatable-and-contractible member contacts the infusion needle to push the infusion needle toward the opening, thereby bending the infusion needle. In this case, preferably, the first inflatable-and-contractible member is composed of a balloon.

The bending means can alternatively be comprised of a guide member which is movably disposed inside the catheter in the vicinity of the opening and which makes contact with the infusion needle; and moving means by which the guide member is moved within the catheter to thereby bend the infusion needle in contact with the guide member. In this case, preferably, the moving means is configured to have a moving wire which is disposed inside the catheter so as to be forwardly and backwardly movable along the axial direction of the catheter and of which a distal portion is engaged with the guide member.

The medical device can also include restoring means by which the infusion needle bent by the bending means is restored into its state before bending. The restoring means can be in the form of a second inflatable-and-contractible member which in a contracted state is disposed inside the catheter so as to be adjacent to the opening and which by being inflated makes contact with the infusion needle in the bent state to push the infusion needle back into its state before bending. In this case, preferably, the second inflatable-and-contractible member is composed of a balloon.

The restoring means may alternatively be a restoring wire which is disposed inside the catheter so as to be forwardly and backwardly movable along the axial direction of the catheter and which by being moved forward has a distal portion brought into contact with the infusion needle in the bent state to push the infusion needle back into its state before bending.

The connecting part which bendably connects the infusion needle to the distal portion of the infusion tubing may be configured to have a bellows structure. Alternatively, the connecting part may have a hinge structure or a so-called joint structure wherein a spherical part is fitted in a recessed socket.

In addition, the connecting part may be formed from a shape memory material, and the bending means may include a coil-formed conductor wound around an outer circumferential portion of the connecting part.

The infusion tubing may be inserted in the catheter so as to be forwardly and backwardly movable along a longitudinal direction of the catheter together with the infusion needle, or may be fixed in the catheter.

According to the medical device disclosed here, the bending means causes the infusion needle connected to the distal portion of the infusion tubing by the connecting part to be bent at the connecting part at essentially a right angle with respect to the distal portion of the infusion tubing. Therefore, the distal portion of the infusion needle can be projected at essentially a right angle with respect to the axial direction of the catheter, and a drug solution can be thereby infused into a brain region.

Another aspect of the disclosure involves a medical device comprising: a catheter with an opening in a side portion of the catheter that opens to outside the catheter; a lumen extending along the catheter and communicating with the opening in the side portion of the catheter; an infusion tubing positioned in the lumen and axially movable along the lumen, the infusion tubing possessing a distal portion; a bendable connecting part connected to the distal portion of the infusion tubing, the bendable connecting part possessing a distal portion; and an infusion needle connected to the distal portion of the bendable connecting part so that the infusion needle and the infusion tubing move together. The bendable connecting part permits the infusion needle to bend relative to the infusion tubing, and the infusion needle possesses an axis and is positionable in a first orientation such that the axis of the infusion needle passes through the catheter at a location other than the opening. A bending piece is located inside the catheter and configured separate from the catheter, with the bending piece being operable to bend the infusion needle located in the first orientation to change the orientation of the infusion needle from the first orientation to a second orientation in which the axis of the infusion needle passes through the opening.

BRIEF DESCRIPTION OF DRAWINGS

FIGS. 4A and 4B show partially longitudinally sectional views having the infusion needle drawn into the longitudinal sectional view of the catheter used in Embodiment 1 showing the structure in the vicinity of the opening of the catheter, wherein FIG. 4A shows the state before bending of the infusion needle, and FIG. 4B shows the state after bending of the infusion needle.

FIGS. 6A and 6B show partially longitudinally sectional views having an infusion needle drawn into a longitudinal sectional view of a catheter used in Embodiment 2 showing a structure in the vicinity of an opening of the catheter, wherein FIG. 6A shows the state before bending of the infusion needle, and FIG. 6B shows the state after bending of the infusion needle.

FIGS. 7A and 7B show partially longitudinally sectional views having an infusion needle drawn into a longitudinal sectional view of a catheter used in Embodiment 3 showing a structure in the vicinity of an opening of the catheter, wherein FIG. 7A shows the state after bending of the infusion needle, and FIG. 7B shows the state upon restoration of the bent infusion needle.

FIGS. 8A to 8C show partially longitudinally sectional views having an infusion needle drawn into a longitudinal sectional view of a catheter used in Embodiment 4 showing a structure in the vicinity of an opening of the catheter, wherein FIG. 8A shows the state during insertion of the infusion needle, FIG. 8B shows the state before bending of the infusion needle, and FIG. 8C shows the state after bending of the infusion needle.

FIGS. 9A and 9B show partially longitudinally sectional views having an infusion needle drawn into a longitudinal sectional view of a catheter used in Embodiment 5 showing a structure in the vicinity of an opening of the catheter, wherein FIG. 9A shows the state after bending of the infusion needle, and FIG. 9B shows the state upon restoration of the bent infusion needle.

FIGS. 11A and 11B show partial lateral views showing an infusion needle with a coil-formed conductor wound around an outer circumferential portion of a connecting part that is used in Embodiment 6, wherein FIG. 11A shows the state before bending of the infusion needle, and FIG. 11B shows the state after bending of the infusion needle.

DETAILED DESCRIPTION

Now, embodiments of the present invention will be described below based on the attached drawings.

Embodiment 1

Figure 1:
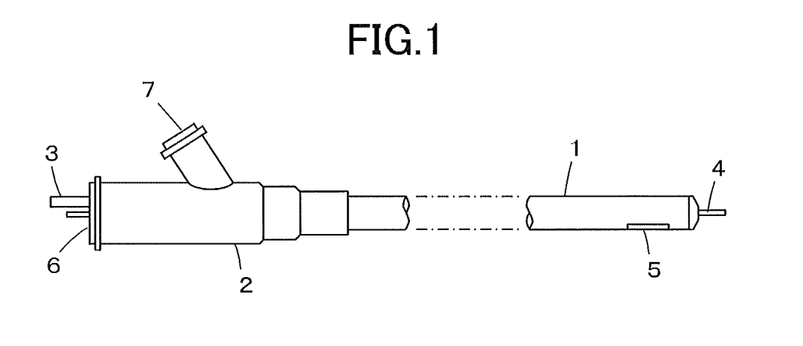
FIG. 1 is a lateral view showing an external appearance of a medical device according to Embodiment 1 of the present invention.

FIG. 1 shows an external appearance of a medical device according to Embodiment 1. The medical device includes a catheter 1, and a branch hub 2 connected to a proximal portion of the catheter 1. The catheter 1 is a member which is to be inserted into a brain region at the time of medical treatment. The catheter 1 has a drug solution infusion tubing 3 and a guide wire 4 inserted inside the catheter to be able to move forward and backward, and also has an opening 5 formed in a side portion near a distal portion of the catheter. On the other hand, the branch hub 2 has an operating port 6 for performing forward and backward movement of the drug solution infusion tubing 3 and the guide wire 4 inserted in the catheter 1 and infusion of a drug solution through the drug solution infusion tubing 3, and a fluid port 7 for inflow/outflow of an inflation fluid into and out of a balloon disposed inside the catheter 1.

Figure 2:
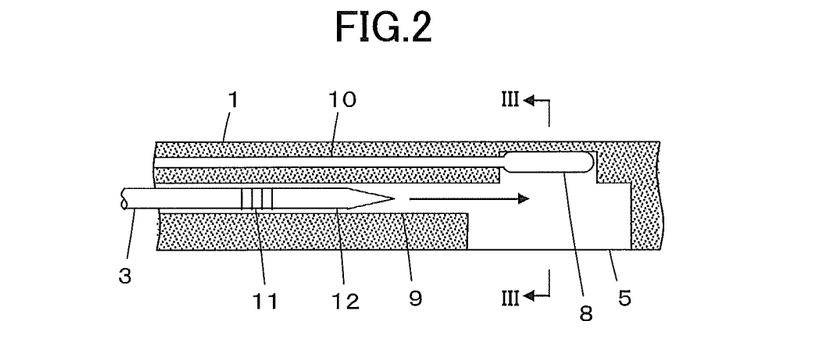
FIG. 2 is a partially longitudinally sectional view having an infusion needle drawn into a longitudinal sectional view of a catheter used in Embodiment 1 showing a structure in the vicinity of an opening of the catheter.

As shown in FIG. 2, in the inside of the catheter 1, a balloon 8 is disposed at such a position as to face the opening 5 and in the state of being contracted inside a side wall on the side opposite to that side portion of the catheter 1 in which the opening 5 is formed. The balloon 8 is inflated in a radial direction of the catheter 1 when the inflation fluid flows into the balloon 8 and is contracted when the inflation fluid flows out from the balloon 8. The balloon 8 constitutes a first inflatable-and-contractible member.

In addition, the catheter 1 is formed therein with a first lumen 9 and a second lumen 10 parallel to each other along an axial direction of the catheter 1. The first lumen 9 is a lumen in which the drug solution infusion tubing 3 is inserted to be able to be moved forward and backward, and of which a proximal portion communicates with the operating port 6 whereas a distal portion communicates with the opening 5. On the other hand, the second lumen 10 is a lumen through which the inflation fluid for driving or inflating the balloon 8 flows, and of which a proximal portion communicates with the fluid port 7 whereas a distal portion communicates with the balloon 8.

With a distal portion of the drug solution infusion tubing 3 inserted in the first lumen 9, an infusion needle 12 communicates through a connecting part 11. The connecting part 11 has a bellows structure so that the infusion needle 12 can be easily bent with respect to the drug solution infusion tubing 3.

Figure 3:
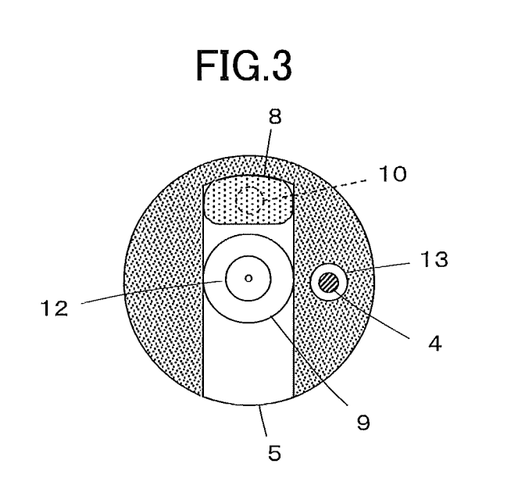
FIG. 3 is an enlarged sectional view taken along a section line III-III of FIG. 2.

Furthermore, as shown in FIG. 3, the catheter 1 is formed therein with a third lumen 13 which extends along the axial direction of the catheter 1 from the operating port 6 to the distal portion of the catheter 1. The guide wire 4 is inserted in the third lumen 13 to be able to be moved forward and backward.

The material forming the catheter 1 is preferably a material which has a certain extent or degree of flexibility. Examples of the material which can be used include thermoplastic resins such as polyolefins such as polyethylene, polypropylene, ethylene-propylene copolymer, ethylene-vinyl acetate copolymer, etc., polyvinyl chloride, polyurethane, polyamides, polyamide elastomers, polyimides, silicone resins, polyether-ether ketone, and polyester elastomers.

In addition, the balloon 8 is preferably formed from a stretchable high-strength polymer. Examples of the material which can be used to form the balloon 8 include polyethylene terephthalate, polyesters (polyethylene terephthalates) obtained by changing a main acid component or a main glycol component of polyethylene terephthalate, mixtures of these polymers, polyamides (nylon 12, nylon 11, MXD6 nylon), and polyarylene sulfides such as PPS (polyphenylene sulfide).

Examples of the material which can be used to form the drug solution infusion tubing 3 and the infusion needle 12 include metals such as stainless steel, aluminum, aluminum alloys, titanium and titanium alloys, and resin materials such as polypropylene, polyvinyl chloride, polyethylene, butadiene-styrene, ABS, polyamides, and polycarbonate.

Embodiment 1

First, as shown in FIG. 1, the guide wire 4 inserted in the third lumen 13 from the operating port 6 protrudes forward from the distal portion of the catheter 1. With the guide wire 4 as a preceding guide, the distal portion of the catheter 1 is inserted into a local part to be medically treated in the brain region or into the vicinity of the local part.

Figure 4A:
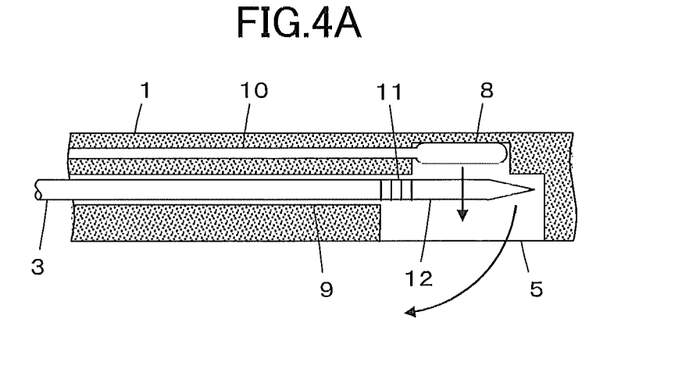

Next, as shown in FIG. 2, the drug solution infusion tubing 3 inserted in the first lumen 9 of the catheter 1 is moved forward. The forward movement of the drug solution infusion tubing 3 is stopped when the infusion needle 12 disposed at the distal portion of the drug solution infusion tubing 3 through the connecting part 11 is located at a position facing the opening 5, as shown in FIG. 4A.

Figure 4B:
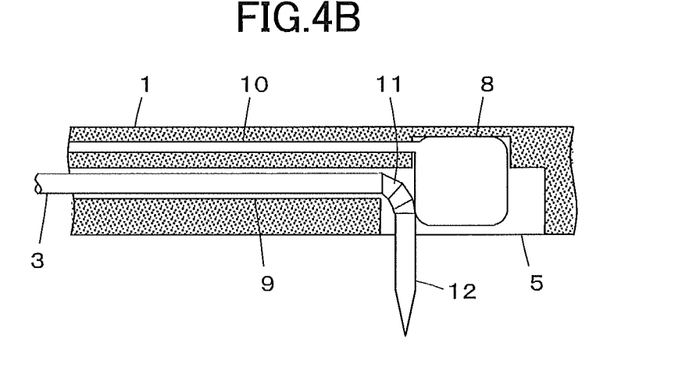

Here, when the inflation fluid is made to flow from the fluid port 7 through the second lumen 10 into the balloon 8 (i.e., when fluid is introduced into the balloon 8), inflation of the balloon 8 is initiated, then the balloon 8 makes contact with the infusion needle 12 and continues inflating while pushing the infusion needle 12 toward the opening 5. As a result, the infusion needle 12 begins to bend at the connecting part 11 with respect to the distal portion of the drug solution infusion tubing 3. When the balloon 8 is inflated to a predetermined size, as shown in FIG. 4B, the infusion needle 12 is bent at essentially a right angle with respect to the distal portion of the drug solution infusion tubing 3. In this instance, since the drug solution infusion tubing 3 extends in the axial direction of the catheter 1, the infusion needle 12 is bent at essentially a right angle with respect to the axial direction of the catheter 1, and a distal portion of the infusion needle 12 projects through the opening 5 to the outside of the catheter 1.

The distal portion of the infusion needle 12 thus projecting to the outside of the catheter 1 at essentially a right angle is able to puncture the local part in the brain region. In this state, the drug solution is supplied through the drug solution infusion tubing 3 into the infusion needle 12, whereby the drug solution is infused via the distal portion of the infusion needle 12 into the local part in the brain region, and medical treatment is performed thereby.

According to Embodiment 1, the distal portion of the infusion needle 12 can be projected at right angle with respect to the axial direction of the catheter 1 by the inflation of the balloon 8. Therefore, positioning of the infusion needle 12 with respect to the local part in the brain region is facilitated. Accordingly, the drug solution can be accurately infused into the local part needing administration of the drug solution, while minimizing the damage to the brain tissue arising from the puncture with the infusion needle 12.

Depending on the status of the local part in the brain region, the drug solution may be delivered (e.g., sprayed, spread, sparged) from the distal portion of the infusion needle 12 set facing the local portion, instead of letting the infusion needle 12 puncture the local part.

When the drug solution infusion tubing 3 is moved backward in relation to the catheter 1 after the medical treatment is finished, the infusion needle 12 is gradually drawn into the first lumen 9 through the connecting part 11 by being pulled by the drug solution infusion tubing 3, and the infusion needle 12 having been bent is restored into its original state. In this state, the catheter 1 is drawn out of the brain region.

Figure 5:
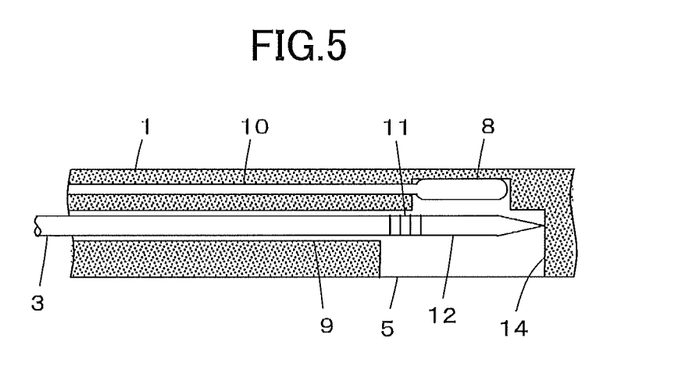
FIG. 5 is a partially longitudinally sectional view having the infusion needle drawn into the longitudinal sectional view of the catheter showing a modification of Embodiment 1 in the state where the infusion needle is inserted.

It is possible to detect or determine that the infusion needle 12 has come to such a position as to face the opening 5 as shown in FIG. 4A in association with the insertion of the drug solution infusion tubing 3 by monitoring the insertion length of the drug solution infusion tubing 3 in relation to the catheter 1, but the method disclosed here is not limited in this regard. For example, the drug solution infusion tubing 3 may be inserted into the first lumen 9 of the catheter 1 while monitoring the feeding pressure of the drug solution infusion tubing 3, and the fact that the distal portion of the infusion needle 12 has come into contact with a wall part 14 formed in the catheter 1 correspondingly to the opening 5 as shown in FIG. 5 may be detected by a change in the feeding pressure to a value not less than a predetermined amount. When the contact of the distal portion of the infusion needle 12 with the wall part 14 is detected, the drug solution infusion tubing 3 is moved backward by a predetermined distance to separate the distal portion of the infusion needle 12 from the wall part 14, and, in this state, the balloon 8 is inflated, whereby the infusion needle 12 can be bent.

Embodiment 2

Figure 6A:
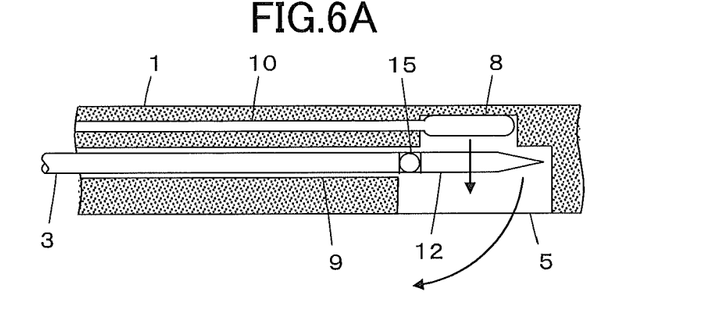

The infusion needle 12 is communicates with the distal portion of the drug solution infusion tubing 3 through the connecting part 11 having the bellows structure in the above-described Embodiment 1, but the infusion needle is not limited to this construction. For instance, as shown in FIG. 6A, the infusion needle 12 may communicate with the distal portion of the drug solution infusion tubing 3 through a connecting part 15 having a hinge structure. The connecting part 15 may have a so-called joint structure wherein a spherical part is fitted in a recessed socket, instead of the hinge structure.

Figure 6B:
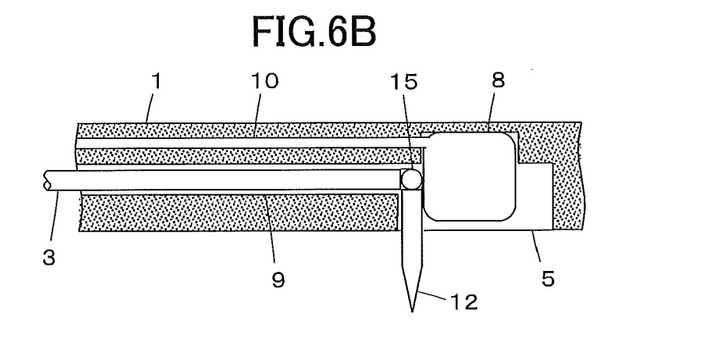

When the balloon 8 is inflated, as shown in FIG. 6B, the infusion needle 12 is bent at essentially a right angle with respect to the distal portion of the drug solution infusion tubing 3 by the connecting part 15. In this instance, since the connecting part 15 has the hinge structure, the infusion needle 12 receiving a pushing force from the balloon 8 (bending means for bending the infusion needle) is easily turned and bent with respect to the distal portion of the drug solution infusion tubing 3, with the connecting part 15 as a center of turning and bending. The balloon 8 is an example of a bending piece that applies a force to the infusion needle 12 (e.g., by contact) while the infusion needle 12 is in a first orientation in which its axis extends through the forward end of the catheter (i.e., the axis of the injection needle does not pass through the opening 5) to bend the infusion needle 12 so that the infusion needle 12 is in a second orientation in which the axis of the infusion needle 12 passes through the opening 5. This bending piece is movable relative to and separate from the catheter (i.e., the bending piece that bends the infusion needle is not constituted by a wall or inner surface of the catheter).

Where the connecting part 15 having the hinge structure is provided with a snap mechanism or a stopper such that the turning angle is stabilized in the state where the infusion needle 12 has been bent at right angle with respect to the distal portion of the drug solution infusion tubing 3, the infusion needle 12 can be bent accurately at a right angle with respect to the axial direction of the catheter 1.

Embodiment 3

Figure 7A:
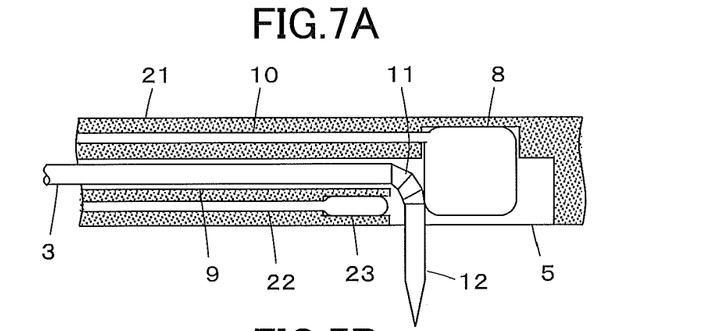

FIG. 7A shows a structure of a major part of a catheter 21 for use in a medical device according to Embodiment 3.

The catheter 21 is the same as the catheter 1 used in Embodiment 1 shown in FIGS. 2 and 3, except that a fourth lumen 22 is further formed along the axial direction of the catheter. The fourth lumen 22 is located on the side opposite to the second lumen 10, with the first lumen 9 interposed between the second lumen 10 and the fourth lumen 22. Inside the catheter 21, a second balloon 23 (restoring means for restoring the infusion needle toward its original pre-bent condition) for restoring the bent infusion needle 12 into its original state is disposed in a contracted state in a part which is adjacent to, and on the side of a proximal portion of the catheter 21 relative to, the opening 5. The balloon 23 is in communication with the fourth lumen 22. The second balloon 23 is formed from the same material as that of the balloon 8 for bending the infusion needle 12. The second balloon 23 is an example of a returning piece that contacts the infusion needle 12 while the infusion needle 12 is in the second orientation in which its axis passes through the opening 5 to return the infusion needle 12 toward the first orientation in which the axis of the infusion needle 12 extends through the forward end of the catheter. The returning piece 23 is movable relative to and separate from the catheter (i.e., the bending/returning piece that bends/returns the infusion needle is not constituted by a wall or inner surface of the catheter).

In addition, like in the catheter 1 used in Embodiment 1, the balloon 8 communicating with the second lumen 10 is disposed at such a position in the catheter 21 as to face the opening 5, and the drug solution infusion tubing 3 is inserted in the first lumen 9.

The bending operation of the infusion needle 12 is the same as in Embodiment 1. Specifically, after the drug solution infusion tubing 3 is moved forward until the infusion needle 12 disposed via the connecting part 11 on the distal portion of the drug solution infusion tubing 3 is located at such a position as to face the opening 5, the balloon 8 is inflated, whereby the infusion needle 12 is bent at essentially a right angle with respect to the distal portion of the drug solution infusion tubing 3, as shown in FIG. 7A. In this instance, the second balloon 23 disposed in the part adjacent to the opening 5 is in the contracted state, so that the second balloon 23 does not obstruct the bending of the infusion needle 12.

Figure 7B:
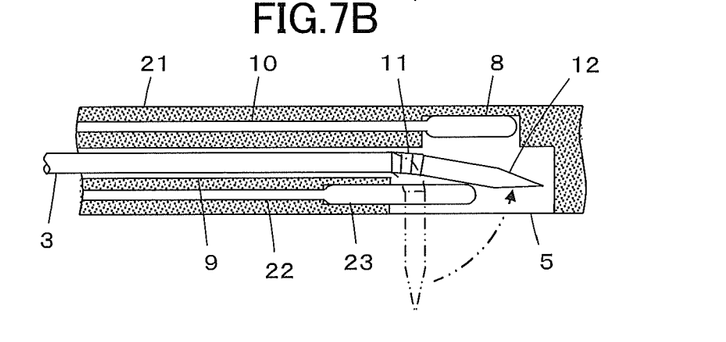

In this state, medical treatment is conducted by infusing or sprinkling the drug solution from the distal portion of the infusion needle 12. When the medical treatment is finished, the balloon 8 having acted to bend the infusion needle 12 is contracted, as shown in FIG. 7B. Then, an inflation fluid is let flow through the fourth lumen 22 into the second balloon 23, to inflate the balloon 23. The second balloon 23 is preliminarily formed so as to inflate in the axial direction of the catheter 21, so that the second balloon 23 thus inflated makes contact with the infusion needle 12 in the bent state and pushes the infusion needle 12 back into its state before bending. Therefore, by moving the drug solution infusion tubing 3 backward in relation to the catheter 21, the infusion needle 12 can be easily drawn into the first lumen 9.

According to Embodiment 3, in addition to yielding effects obtained in the above-described Embodiment 1, it is possible to reduce the amount of friction between an inner surface of the catheter 21 and the connecting part 11 and the infusion needle 12 during the backward movement of the drug solution infusion tubing 3.

In Embodiment 3, also, like in Embodiment 2 shown in FIGS. 6A and 6B, the infusion needle 12 communicating with the distal portion of the drug solution infusion tubing 3 through the connecting part 15 having the hinge structure can be used.

While the drug solution infusion tubing 3 is inserted in the first lumen 9 of the catheter 1 or 21 so as to be able to be moved forward and backward in the above-described Embodiments 1 to 3, the medical device is not limited in this regard. As long as the infusion needle 12 can be bent at essentially a right angle with respect to the axial direction of the catheter by inflating the balloon 8, the drug solution infusion tubing 3 may be fixed in the catheter 1 or 21 in the state in which the infusion needle 12 is located so as to face the opening 5, as shown in FIG. 4A for example. In this case, a configuration can be adopted in which, instead of using the independent drug solution infusion tubing 3, the first lumen 9 is allowed to function as a drug solution infusion tubing and the infusion needle 12 communicates with the distal portion of the first lumen 9 through the connecting part 11 or 15.

Embodiment 4

Figure 8A:
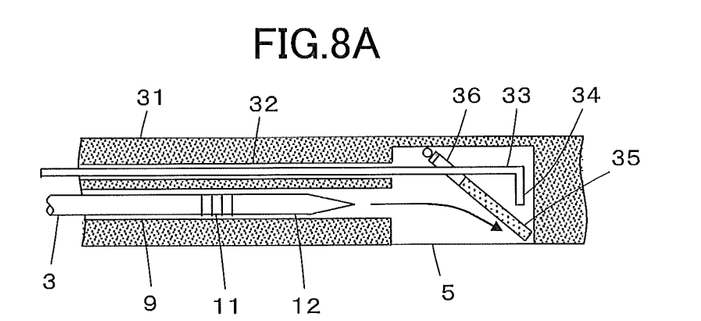

FIG. 8A shows a structure of a major part of a catheter 31 for use in a medical device according to Embodiment 4.

Like the catheter 1 used in Embodiment 1 shown in FIGS. 2 and 3, the catheter 31 has the opening 5 formed in the side portion near the distal portion of the catheter 31, and has the first lumen 9 extending along the axial direction of the catheter 31 from a proximal portion to the opening 5 of the catheter 31. Furthermore, the catheter 31 is formed with a fifth lumen 32 extending parallel to the first lumen 9 from the proximal portion to the opening 5 of the catheter 31. A moving wire 33 is positioned in the fifth lumen 32 so as to be able to be moved forward and backward. A distal end of the moving wire 33 is located inside the opening 5, and a bent part 34 bent in an L-shape is formed at the distal end.

In addition, in the inside of the catheter 31, a flat plate-like guide member 35 is turnably hinged to an inner surface located so as to face the opening 5 and on the side opposite to that side portion of the catheter 31 in which the opening 5 is formed. A through-hole 36 is provided inside the guide member 35, and the moving wire 33 passes through the through-hole 36. The through-hole 36 has a sufficient size such that the moving wire 33 does not make contact with the guide member 35 even when the guide member 35 is turned.

The catheter 31 can be formed from the same material as that of the catheter 1 used in Embodiment 1.

In operation, first, the drug solution infusion tubing 3 with the infusion needle 12 communicating with the distal portion of the drug solution infusion tubing 3 through the connecting part 11 is inserted in the first lumen 9, and is moved forward. In this instance, as shown in FIG. 8A, the guide member 35 is so situated as to have its end portion on the opening 5 side in a state of having been turned toward the distal end of the catheter 31, and is inclined with respect to the axial direction of the catheter 31.

Figure 8B:
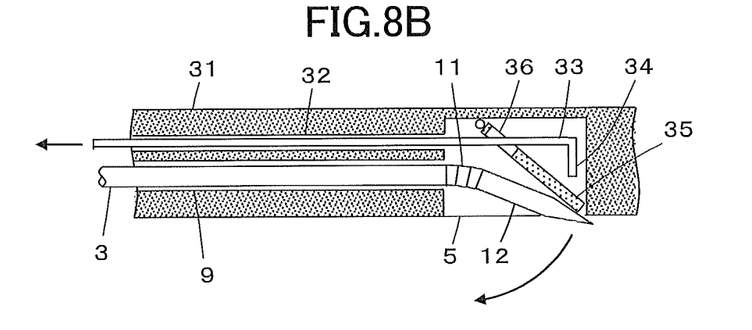

Attendant on the forward movement of the drug solution infusion tubing 3, the distal portion of the infusion needle 12 comes into contact with a surface of the guide member 35. In this case, since the guide member 35 is inclined, as shown in FIG. 8B, the infusion needle 12 is guided by the surface of the guide member 35, to be put into a state of being bent slightly at the connecting part 11 toward the opening 5.

Figure 8C:
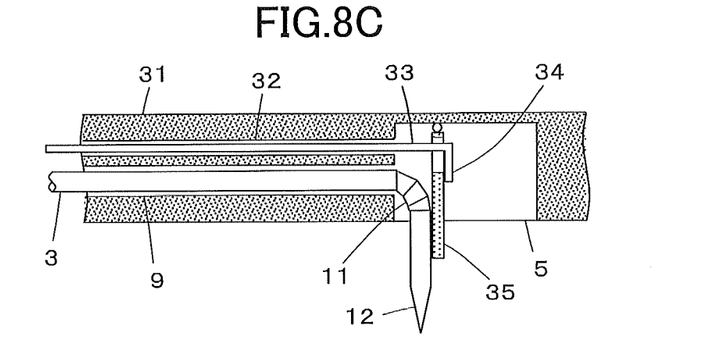

Here, when the forward movement of the drug solution infusion tubing 3 is finished and the moving wire 33 (moving means by which the guide member 35 is moved within the catheter) is moved backward toward the proximal portion with respect to the catheter 31, as shown in FIG. 8C, the bent part 34 formed at the distal end of the moving wire 33 makes contact with a back surface of the guide member 35 and turns the guide member 35, whereby the infusion needle 12 is pushed by the guide member 35 (bending means for bending the infusion needle) and, further, is bent at the connecting part 11. The guide member 35 is another example of a bending piece that applies a force to the infusion needle 12 (e.g., by contact) while the infusion needle 12 is in a first orientation in which its axis extends through the forward end of the catheter (i.e., the axis of the injection needle does not pass through the opening 5) to bend the infusion needle 12 to a second orientation in which the axis of the infusion needle 12 passes through the opening 5. This bending piece 35 is movable relative to and separate from the catheter (i.e., the bending piece that bends the infusion needle is not constituted by a wall or inner surface of the catheter).

In this manner, the infusion needle 12 can be bent at essentially a right angle with respect to the axial direction of the catheter 31 to project the distal portion of the infusion needle 12 to the outside of the catheter 31.

Embodiment 5

Figure 9A:
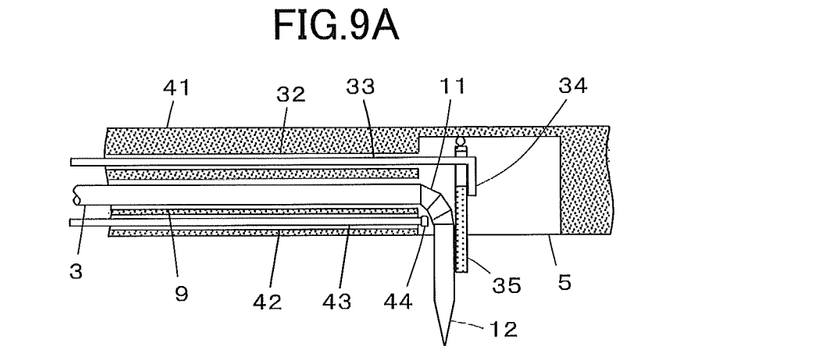

FIG. 9A shows a structure of a major part of a catheter 41 for use in a medical device according to Embodiment 5.

Figure 10:
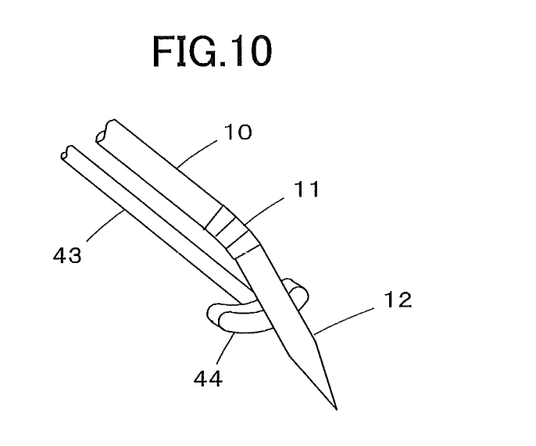
FIG. 10 is a perspective view of a contact member used in Embodiment 5.

The catheter 41 is the same as the catheter 31 used in Embodiment 4 shown in FIG. 8A, except that, further, a sixth lumen 42 is formed along the axial direction of the catheter, and a restoring wire 43 for restoring the bent infusion needle 12 into its original state is inserted in the sixth lumen 42 so as to be able to be moved forward and backward. The sixth lumen 42 is located on the side opposite to the fifth lumen 32 with the first lumen 9 interposed between the sixth lumen 42 and the fifth lumen 32, and extends from a proximal portion to the opening 5 of the catheter 41. Furthermore, at a distal portion of the restoring wire 43 facing the opening 5, a contact member 44 having an arcuate shape is fixed, as shown in FIG. 10.

In addition, like in the catheter 31 used in Embodiment 4, the flat plate-like guide member 35 is turnably disposed at such a position as to face the opening 5, the moving wire 33 is inserted in the fifth lumen 32 so as to be able to be moved forward and backward, and the drug solution infusion tubing 3 is positioned in the first lumen 9.

The bending operation of the infusion needle 12 is the same as in Embodiment 4. Specifically, after the drug solution infusion tubing 3 is moved forward until the infusion needle 12 disposed via the connecting part 11 on the distal portion of the drug solution infusion tubing 3 is located at such a position as to face the opening 5, the moving wire 33 is moved backward toward the proximal portion, whereby the infusion needle 12 is pressed by the guide member 35, to be bent at essentially a right angle with respect to the distal portion of the drug solution infusion tubing 3, as shown in FIG. 9A. In this instance, the restoring wire 43 with the contact member 44 (restoring means for restoring the infusion needle toward its original pre-bent condition) fixed to the distal portion thereof is in a state of having been moved backward relative to the catheter 41, so that the restoring wire 43 does not obstruct the bending of the infusion needle 12.

Figure 9B:
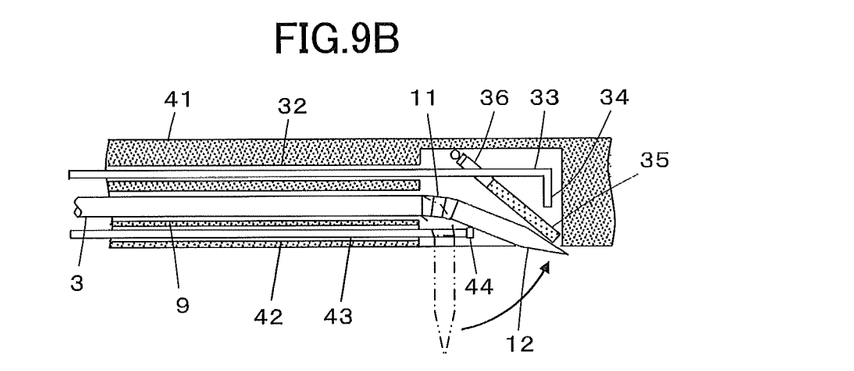

In this state, medical treatment is conducted by infusing or sprinkling the drug solution from the distal portion of the infusion needle 12. When the medical treatment is finished, the moving wire 33 having acted to bend the infusion needle 12 is moved forward toward the distal portion of the catheter 41 and the restoring wire 43 is moved forward, as shown in FIG. 9B. As a result, the contact member 44 fixed to the distal portion of the restoring wire 43 makes contact with the infusion needle 12 in the bent state, and the infusion needle 12 is pushed back into its state before bending. Therefore, by moving the drug solution infusion tubing 3 backward in relation to the catheter 41, the infusion needle 12 can be rather easily drawn into the first lumen 9. The contact member 44 is another example of a returning piece that contacts the infusion needle 12 while the infusion needle 12 is in the second orientation in which its axis passes through the opening 5 to return the infusion needle 12 toward the first orientation in which the axis of the infusion needle 12 extends through the forward end of the catheter.

According to Embodiment 5, in addition to yielding effects obtained in the above-described Embodiment 4, it is possible to reduce the amount of friction between the inner surface of the catheter 41 and the connecting part 11 and the infusion needle 12 during the backward movement of the drug solution infusion tubing 3.

Embodiment 6

The infusion needle 12 is bent by the inflation of the balloon 8 in the above-described Embodiments 1 to 3, and the infusion needle 12 is bent by use of the moving wire 33 and the guide member 35 in Embodiments 4 and 5. The medical device is not restricted in this way. For example, a configuration may be adopted in which, as shown in FIG. 11A, the drug solution infusion tubing 3 and the infusion needle 12 communicate with each other through a connecting part 51 formed from a shape memory material, and a coil-formed conductor 52 is wound around an outer circumferential portion of the connecting part 51.

The connecting part 51 has preliminarily been treated for shape memory such that it has a straight tubular shape extending rectilinearly in temperature environments of not higher than a predetermined threshold value, for example, at normal temperature, and the connecting part 51 has an L-shaped tubular shape with one end directed at a right angle with respect to the other end in temperature environments above the predetermined threshold value.

Figure 11A:
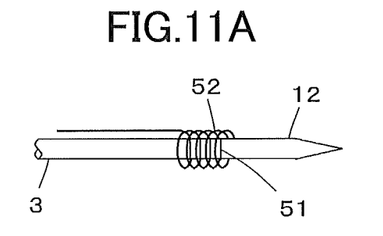
Figure 11B:
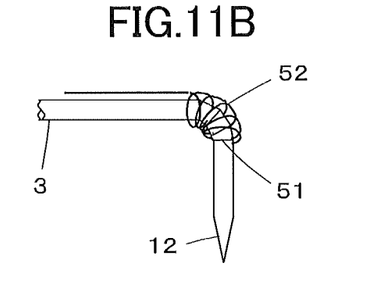

Therefore, when no current is passed through the coil-formed conductor 52, a normal temperature environment is maintained, so that the drug solution infusion tubing 3 and the infusion needle 12 are interconnected rectilinearly through the straight tubular connecting part 51, as shown in FIG. 11A. On the other hand, when a current is passed through the coil-formed conductor 52 to heat the connecting part 51 to a temperature above the predetermined threshold value, the connecting part 51 (bending means for bending the infusion needle) is deformed into the L-shaped tubular shape, whereby the infusion needle 12 is bent at essentially a right angle with respect to the distal portion of the drug solution infusion tubing 3, as shown in FIG. 11B.

By use of such connecting part 51 and coil-formed conductor 52, also, like in Embodiments 1 to 5, the infusion needle 12 can be bent at essentially a right angle with respect to the axial direction of the catheter. The conductor 52 is an example of a bending piece that is operable to bend the infusion needle 12 while the infusion needle 12 is in a first orientation in which its axis extends through the forward end of the catheter (i.e., the axis of the injection needle does not pass through the opening 5) so that the infusion needle 12 is oriented in a second orientation in which the axis of the infusion needle 12 passes through the opening 5. The bending piece 52 is movable relative to and separate from the catheter (i.e., the bending piece 52 that bends the infusion needle is not constituted by a wall or inner surface of the catheter).

In addition, by only stopping the supply of current to the coil-formed conductor 52 to thereby lower the temperature of the connecting part 51 to or below the predetermined threshold value, the connecting part 51 is returned into the straight tubular shape and, therefore, the bent infusion needle 12 can be restored into its state before bending. The conductor 52 is an example of a bending piece that forces the infusion needle 12, while the infusion needle 12 is in a first orientation in which its axis extends through the forward end of the catheter (i.e., the axis of the injection needle does not pass through the opening 5), to bend so that the infusion needle 12 is in a second orientation in which the axis of the infusion needle 12 passes through the opening 5.

A configuration may also be adopted in which the coil-formed conductor 52 is preliminarily wound around the outer circumferential portion of the connecting part 51 and is moved forward and backward within the catheter together with the connecting part 51 in association with the forward and backward movement of the drug solution infusion tubing 3 in relation to the catheter. Or, a configuration may also be adopted in which the coil-formed conductor 52 is preliminarily fixed in the opening of the catheter, and, when the drug solution infusion tubing 3 is moved forward until the infusion needle 12 is located at such a position as to face the opening of the catheter, the infusion needle 12 and the connecting part 51 are inserted into the inside of the coil-formed conductor 52 with the result that the coil-formed conductor 52 is located around the outer circumferential portion of the connecting part 51.

While the distal portion of the infusion needle 12 projects through the opening 5 to the outside of the catheter when the infusion needle 12 is bent at essentially a right angle with respect to the axial direction of the catheter in the above-described Embodiments 1 to 6, this is not restrictive. When the infusion needle 12 is bent, the distal portion of the infusion needle 12 may not project to the outside of the catheter, but may remain inside the catheter in a posture of facing the outside through the opening 5. In this state, the drug solution can be infused or delivered (e.g., sprayed, spread, sparged) to the site of medical treatment.

The detailed description above describes embodiments of the medical device disclosed here. The invention is not limited, however, to the precise embodiments and variations described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A medical device characterized by comprising:
 a catheter having an opening passing through a circumferential wall of the catheter;
 an infusion tubing extending within the catheter in an axial direction of the catheter, the infusion tubing possessing a distal portion;
 an infusion needle disposed at the distal portion of the infusion tubing;
 a bendable connecting part connecting the infusion needle to the distal portion of the infusion tubing; and
 bending means for bending the infusion needle, located inside the catheter in facing relation to the opening, at the connecting part at substantially a right angle with respect to the distal portion of the infusion tubing, and the bending means causing the infusion needle to project from inside the catheter to outside the catheter through the opening.

2. The medical device according to claim 1, wherein the bending means includes a first inflatable-and-contractible member which in a contracted state is disposed inside the catheter so as to face the opening with the infusion needle therebetween and which when inflated makes contact with the infusion needle to push the infusion needle toward the opening, thereby bending the infusion needle.

3. The medical device according to claim 1, wherein the bending means includes:
 a guide member which is movably disposed inside the catheter in the vicinity of the opening and which makes contact with the infusion needle; and moving means for moving the guide member within the catheter to contact the infusion needle and bend the infusion needle.

4. The medical device according to claim 3, wherein the moving means includes a wire movably positioned within the catheter to move forwardly and rearwardly along an axial direction of the catheter, the wire possessing a distal portion engaged with the guide member.

5. The medical device according to claim 1, further comprising restoring means for restoring the infusion needle bent by the bending means to a state of the infusion needle before bending.

6. The medical device according to claim 5, wherein the restoring means includes a second inflatable-and-contractible member which in a contracted state is disposed inside the catheter adjacent the opening and which upon being inflated makes contact with the infusion needle in a bent state to push the infusion needle back into the infusion needle's state before bending.

7. The medical device according to claim 5, wherein the restoring means includes a restoring wire which is disposed inside the catheter so as to be forwardly and backwardly movable along an axial direction of the catheter and which by being moved forward has a distal portion brought into contact with the infusion needle in the bent state to push the infusion needle back into its state before bending.

8. The medical device according to claim 1, wherein the connecting part is formed from a shape memory material, and the bending means includes a coil-formed conductor wound around an outer circumferential portion of the connecting part.

9. The medical device according to claim 1, wherein the infusion tubing is positioned in the catheter to be forwardly and rearwardly movable, together with the infusion needle, along a longitudinal direction of the catheter.

10. The medical device according to claim 1, wherein the infusion tubing is fixed in the catheter.

11. A medical device comprising:
a catheter with an opening in a side portion of the catheter that opens to outside the catheter, the catheter possessing a distal-most end, the opening in the side portion of the catheter being spaced proximally from the distal-most end of the catheter;
a lumen extending along the catheter and communicating with the opening in the side portion of the catheter;
an infusion tubing positioned in the lumen and axially movable along the lumen, the infusion tubing possessing a distal portion;
a bendable connecting part connected to the distal portion of the infusion tubing, the bendable connecting part possessing a distal portion;
an infusion needle connected to the distal portion of the bendable connecting part so that the infusion needle and the infusion tubing move together, the bendable connecting part permitting the infusion needle to bend relative to the infusion tubing, the infusion needle possessing an axis and being positionable in a first orientation such that the axis of the infusion needle passes through the catheter at a location other than the opening; and
a bending piece located inside the catheter and configured separate from the catheter, the bending piece being operable to bend the infusion needle located in the first orientation to change the orientation of the infusion needle from the first orientation to a second orientation in which the axis of the infusion needle passes through the opening.

12. The medical device according to claim 11, wherein the lumen is a first lumen, and further comprising a second lumen spaced from the first lumen, the bending piece comprising an inflatable balloon which receives fluid by way of the second lumen to inflate the balloon to an inflated state in which the balloon contacts the infusion needle to bend the infusion needle from the first orientation to the second orientation.

13. The medical device according to claim 11, wherein the bending piece comprises an inflatable balloon which contacts the infusion needle upon being inflated to bend the infusion needle from the first orientation to the second orientation.

14. The medical device according to claim 11, wherein the connecting part comprises a hinge structure.

15. The medical device according to claim 11, further comprising an inflatable balloon which is inflatable to move the infusion needle from the second orientation back towards the first orientation, the infusion needle being located between the inflatable balloon and the bending piece.

16. The medical device according to claim 11, wherein the bending piece comprises a guide member positioned in an inclined manner relative to the infusion needle, the guide member including a through hole, and including a wire member passing through the through hole and axially movable to move the guide member to a position in which the guide member bends the infusion needle to the second orientation.

17. The medical device according to claim 16, wherein the lumen is one lumen, and the medical device includes an other lumen in the catheter, the wire member being positioned in the other lumen.

18. The medical device according to claim 17, further comprising an axially movable restoring wire to which is connected a contact member so that the restoring wire and the contact member move together, the contact member being positioned to contact the infusion needle located in the second orientation and move the infusion needle back towards the first orientation, the restoring wire being movably positioned in an additional lumen in the catheter, the additional lumen being spaced from the one lumen and the other lumen.

19. The medical device according to claim 11, further comprising an axially movable restoring wire to which is connected a contact member so that the restoring wire and the contact member move together, the contact member being positioned to contact the infusion needle located in the second orientation to move the infusion needle back towards the first orientation.

20. The medical device according to claim 11, wherein the bendable connecting part is made of a shape memory material, and the bending piece comprises a coil conductor surrounding the bendable connecting part made of the shape memory material so that current supplied to the coil causes the bendable connecting part made of the shape memory material to bend and move the infusion needle toward the second orientation.

21. The medical device according to claim 1, wherein a distal portion of the bending means is located in the catheter, and the bendable connecting part is in the catheter when the bending means bend the infusion needle at the connecting part.

22. The medical device according to claim 1, wherein the infusion needle is located between a proximal portion of the opening and the bending means after the bending means projects the infusion needle to outside of the catheter.

23. A medical device comprising:
a catheter possessing a circumferential wall, the catheter comprising an opening passing through the circumferential wall of the catheter and opening to outside the catheter;

a lumen extending along the catheter and communicating with the opening in the side portion of the catheter;

a tubing positioned in the lumen and axially movable along the lumen, the tubing possessing a distal portion;

a bendable connecting part connected to the distal portion of the tubing, the bendable connecting part possessing a distal portion;

a member connected to the distal portion of the bendable connecting part so that the member and the tubing move together, the bendable connecting part permitting the member to bend relative to the tubing, the member possessing an axis and being positionable in a first orientation such that the axis of the member passes through the catheter at a location other than the opening; and a bending piece located inside the catheter and configured separate from the catheter, the bending piece being operable to bend the member located in the first orientation to change the orientation of the member from the first orientation to a second orientation in which the axis of the member passes through the opening.

24. The medical device according to claim 23, wherein the member is located between a proximal portion of the opening and the bending piece after the bending piece bends the member to change the orientation of the member from the first orientation to the second orientation.

* * * * *